(12) United States Patent
Traversaz et al.

(10) Patent No.: US 10,589,020 B2
(45) Date of Patent: Mar. 17, 2020

(54) HOLDING DEVICE FOR A SYRINGE PUMP

(71) Applicant: Fresenius Vial SAS, Brezins (FR)

(72) Inventors: Philippe Traversaz, Saint-Blaise du Buis (FR); Florie Perrigouard, La Tronche (FR); Roman Barthelemy, Eybens (FR); Fabien Thomas, Meyrie (FR)

(73) Assignee: Fresenius Vial SAS, Brézins (FR)

( * ) Notice: Subject to any disclaimer, the term of this patent is extended or adjusted under 35 U.S.C. 154(b) by 264 days.

(21) Appl. No.: 15/027,613

(22) PCT Filed: Oct. 22, 2014

(86) PCT No.: PCT/EP2014/072619
§ 371 (c)(1),
(2) Date: Apr. 6, 2016

(87) PCT Pub. No.: WO2015/062926
PCT Pub. Date: May 7, 2015

(65) Prior Publication Data
US 2016/0250410 A1    Sep. 1, 2016

(30) Foreign Application Priority Data

Nov. 4, 2013 (EP) ..................................... 13306515

(51) Int. Cl.
*A61M 5/14* (2006.01)
*A61M 5/145* (2006.01)
(Continued)

(52) U.S. Cl.
CPC ........ *A61M 5/1413* (2013.01); *A61M 5/1415* (2013.01); *A61M 5/1452* (2013.01);
(Continued)

(58) Field of Classification Search
CPC ........ A61M 2205/14; A61M 2205/332; A61M 5/14546; A61M 5/1456; A61M 5/1458; Y10S 128/01
See application file for complete search history.

(56) References Cited

U.S. PATENT DOCUMENTS

| | | | |
|---|---|---|---|
| 4,769,009 A * | 9/1988 | Dykstra | A61M 1/3672 128/DIG. 1 |
| 5,232,449 A * | 8/1993 | Stern | A61M 5/1456 128/DIG. 1 |

(Continued)

FOREIGN PATENT DOCUMENTS

| | | |
|---|---|---|
| EP | 1362606 A1 | 11/2003 |
| EP | 2345441 A1 | 7/2011 |

(Continued)

OTHER PUBLICATIONS

International Search Report and Written Opinion, counterpart International Appl No. PCT/EP2014/072619, dated Jan. 19, 2015.

*Primary Examiner* — Scott J Medway
(74) *Attorney, Agent, or Firm* — Cook Alex Ltd.

(57) ABSTRACT

The invention relates to a holding device for a syringe pump, the holding device being configured for holding the barrel of a syringe and comprising a rotatable holding member (11) which is rotatable from an open into a closed position, wherein the holding member (11) is configured in such a way that in the closed position the syringe barrel will be secured between a portion of the rotatable holding member (11) and a fixed section of the syringe pump. According to the invention, a damping device (2) configured to dampen the movement of the rotatable holding member (11) from the open into the closed position.

19 Claims, 4 Drawing Sheets

(51) Int. Cl.
  *A61M 5/142*    (2006.01)
  *F16M 13/02*    (2006.01)
(52) U.S. Cl.
  CPC ...... *A61M 5/1456* (2013.01); *A61M 5/14216* (2013.01); *F16M 13/02* (2013.01); *A61M 2005/14506* (2013.01); *A61M 2209/086* (2013.01)

(56) References Cited

U.S. PATENT DOCUMENTS

| | | | |
|---|---|---|---|
| 6,592,551 B1 * | 7/2003 | Cobb | A61M 5/1456 128/DIG. 1 |
| 7,153,290 B2 | 12/2006 | Wakabayashi | |
| 2008/0225440 A1 * | 9/2008 | Nemoto | H01H 3/20 360/319 |

FOREIGN PATENT DOCUMENTS

| | | | | |
|---|---|---|---|---|
| FR | 2911662 A1 | 7/2008 | | |
| GB | 19812 A | 4/1907 | | |
| GB | 2434738 A | 8/2007 | | |
| WO | PCT-WO2005/102416 A1 | 11/2005 | | |
| WO | WO-2005102416 A1 * | 11/2005 | ........ | A61M 5/14546 |

* cited by examiner

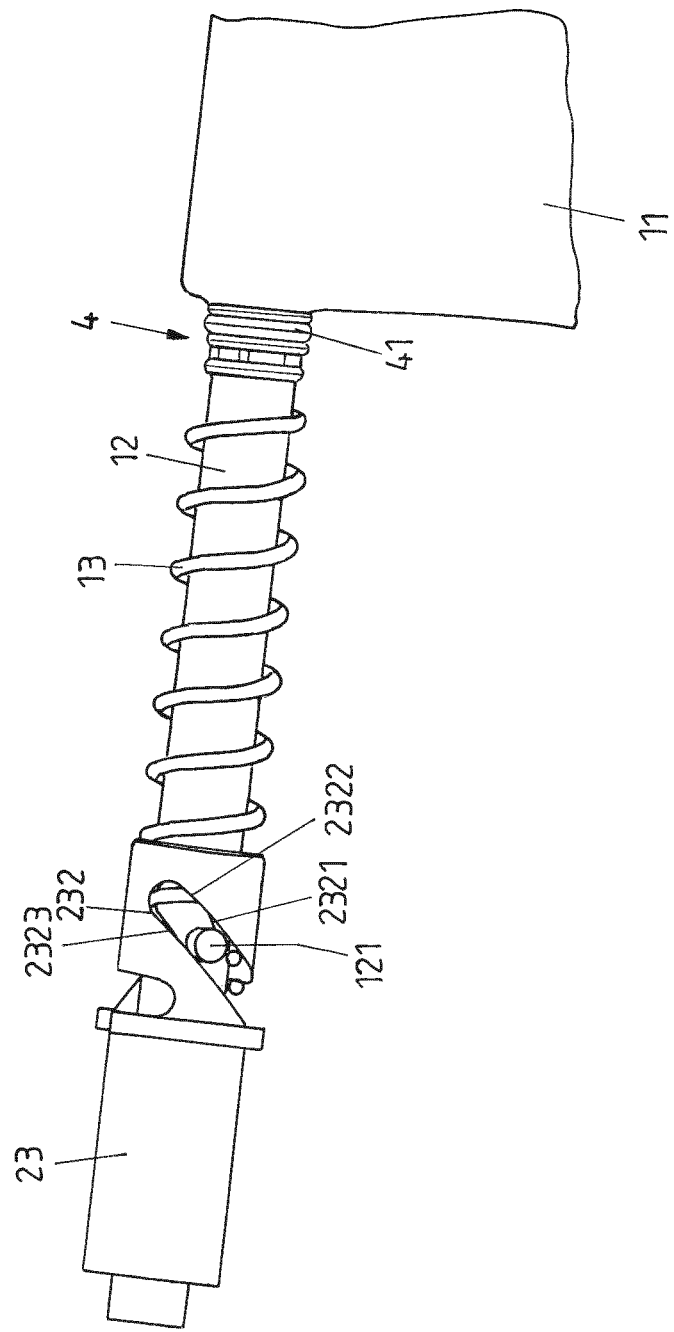

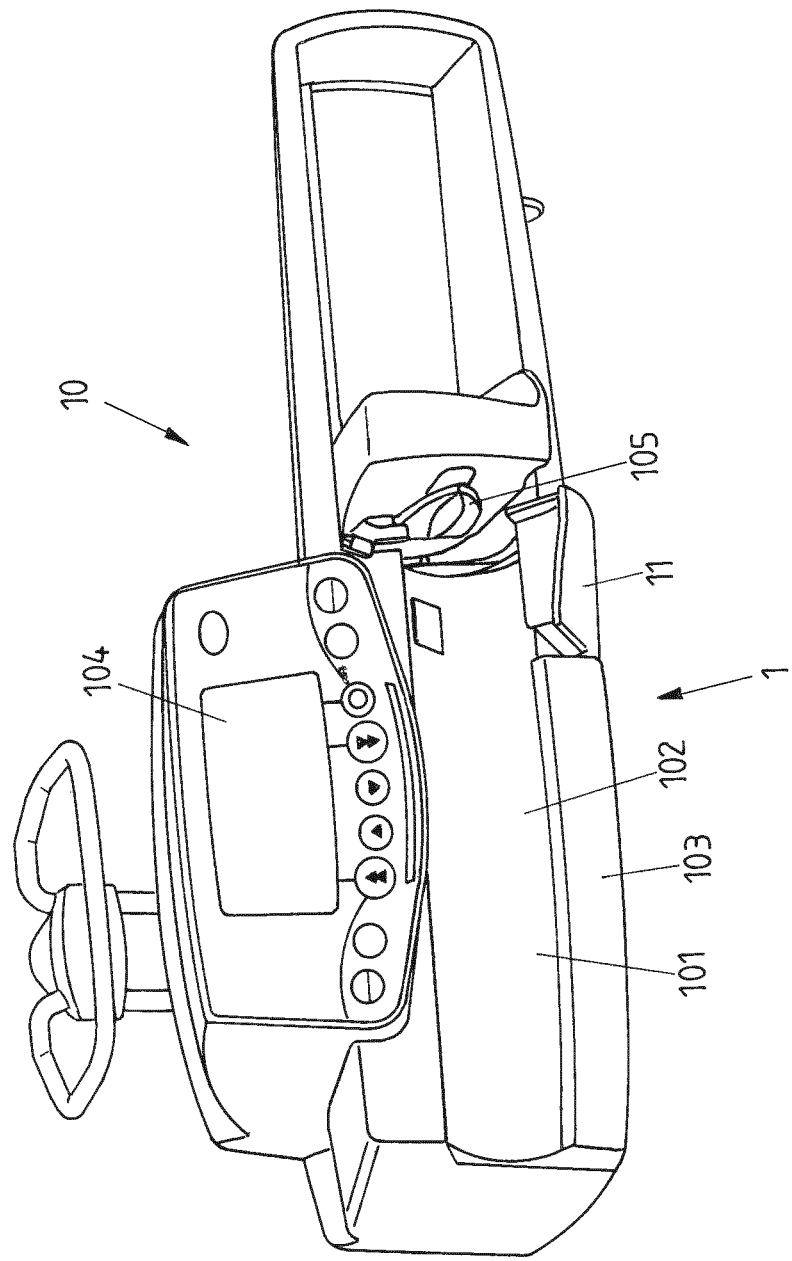

HOLDING DEVICE FOR A SYRINGE PUMP

The present application is a U.S. National Stage of PCT International Patent Application No. PCT/EP2014/1072619, filed Oct. 22, 2014, which claims priority to EP Application No. 13306515.1, filed Nov. 4, 2013, both of which are hereby incorporated herein by reference.

BACKGROUND

The invention relates to a holding device for a syringe pump.

A variety of mechanism is known for fixing a syringe to a syringe pump. For example, a syringe pump has a receiving section for receiving the barrel of a syringe, wherein a rotatable claw is used to fix the barrel to the receiving section as disclosed in U.S. Pat. No. 7,153,290 B2. Further, WO 2005/102416 discloses that two claws are used for mounting a syringe barrel to an injection device.

It is an object of the invention to provide a holding device for a syringe pump that securely fixes a syringe barrel to a syringe pump and at the same time keeps the risk that the syringe will be damaged by the holding device as low as possible.

SUMMARY

According to the invention, a holding device for a syringe pump is provided, the holding device being configured for holding the barrel of a syringe and comprising:
- a rotatable holding member which is rotatable from an open into a closed position,
- wherein the holding member is configured in such a way that in the closed position the syringe barrel will be secured between a portion of the rotatable holding member and a fixed section of the syringe pump; and
- a damping device configured to dampen the movement of the rotatable holding member from the open into the closed position.

The damping device thus slows down the closing movement of the holding member such that it counteracts potential damage to the syringe (in particular the syringe barrel) during the closure movement of the holding member. The "fixed section" of the syringe pump may be a portion of a receiving section of the syringe pump for receiving the syringe barrel such that the syringe barrel may be clamped between the rotatable holding member and the portion of the receiving section. The receiving section and thus the "fixed section" is not movable (in particular not rotatable) with respect to other parts (such as a housing) of the syringe pump. Thus, using the holding device according to the invention, the syringe barrel will be secured to the syringe pump by a single movable holding member, only.

For example, the holding device comprises a spring configured to bias (pre-tension) the holding member against the syringe barrel. In particular, the spring has a rather high spring constant (e.g. using a spring of rather high stiffness) such that the holding member may exert a rather high clamping force to the syringe barrel to securely fix the barrel to the syringe pump. In particular, the spring properties may be chosen in such a way that the EN 60601-2-24 Ed. 3 standard is met. For example, the spring is configured in such a way that an (axial) force of at least 15N has to be exerted to the syringe for at least 15 s for taking out the syringe.

Further, even if the spring has a high spring constant such that the holding member will exert a rather high clamping force on the syringe barrel in the closed position, the damping device (e.g. in the form of a shock absorber) thwarts damage to the syringe (in particular to the barrel of smaller syringes) since it slows down the rotation of the holding member during the closing movement in that it absorbs part of the kinetic energy of the holding member such that the impact on the syringe barrel is reduced.

The holding device may comprise a shaft connected to the holding member and thus rotating along with the holding member, wherein the spring may be a coil spring surrounding shaft. The coil spring may be arranged in such a way that during the closing movement of the holding member a torque is exerted on the spring. However, the spring may also interact with the holding member (or other components of the holding device) in such a way that an axial force is exerted on the spring when the holding member is pivoted into the closed position. Further, it is also conceivable that other types of springs are used.

According to another embodiment of the invention, the damping device comprises a first and a second toothed element in engagement with one another. In particular, the rotatable holding member interacts with the first toothed element (e.g. a braked gear wheel) via the second toothed element (e.g. a gear rack) in such a way that during the closing rotation of the holding member the first and the second toothed element will move relative to one another such that due to, for example, frictional or viscous forces (e.g. between the toothed elements or exerted on the first toothed element) the rotational movement of the holding member is slowed down.

For example, the second toothed element interacts with the holding member in such a way that it moves linearly when the holding member is rotated from the open into the closed position. In particular, the second toothed element is a gear rack engaging a first toothed element in the form of a braked gear wheel, i.e. a gear wheel that comprises a braking device that counteracts a rotation of the gear wheel. For example, the braking device of the braked gear wheel comprises a viscous fluid such that a rotation of the gear wheel and thus of the holding member is slowed down due to viscous forces.

However, damping forces can also be created by other means such as air compression. For example, the damping device comprises a friction element, a hydraulic jack or a pneumatic jack, wherein these components may interact with the braked gear wheel. However, it is also conceivable that at least one of these components is provided instead of the braked gear wheel. For example, the friction element, the hydraulic jack or the pneumatic jack interact with the shaft connected to the holding member in such a way that friction forces, hydraulic forces or pneumatic forces act on the shaft that slow down the rotation of the holding member into the closed position.

According to another exemplary embodiment of the invention, the holding device comprises a shaft rotating along with the rotatable holding member (as already mentioned above) and a cam element connected to the gear rack, wherein the shaft engages the cam element in such a way that the cam element and thus the gear rack is linearly moved when the rotatable holding member is rotated from the open into the closed position.

More particularly, the shaft comprises a protrusion engaging a contact surface of the cam element. For example, the protrusion extends radially (i.e. perpendicular to the shaft axis), e.g. as a radially extending pin.

The contact surface of the cam element may be orientated obliquely with respect to the shaft axis; for example, the contact surface extends under an angle of about 45° with respect to the shaft axis. The cam element may comprise a hollow body at least partially surrounding the shaft, wherein the contact surface is formed by an edge of a (e.g. slit-like) recess in the hollow body.

Further, the holding member may comprise a concave surface portion adapted to the cylindrical form of a syringe barrel. Moreover, the holding device according to the invention may comprise attachment structures for attaching the holding device to a part of a syringe pump. For example, the holding device comprises attachment holes for receiving screws or rivets or other attachment elements.

The invention also relates to a syringe pump comprising a holding device as described above.

BRIEF DESCRIPTION OF THE DRAWINGS

Embodiments of the invention are described in more detail hereinafter with reference to the drawings. These show:

FIG. 3 a perspective view of the cam tube and the spring section of the holding device of FIG. 1; and FIG. 4 a perspective view of a syringe pump comprising a holding device according to the invention.

DETAILED DESCRIPTION OF THE EMBODIMENTS

Figure 1:
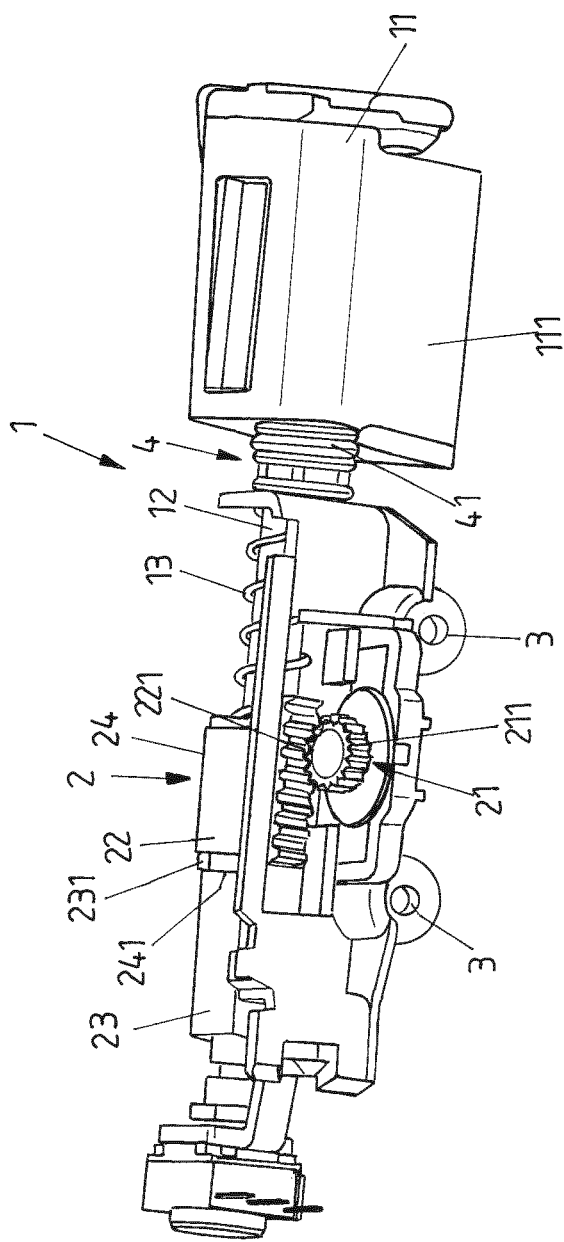
FIG. 1 a perspective view of a holding device for a syringe pump according to an embodiment of the invention.
Figure 2:
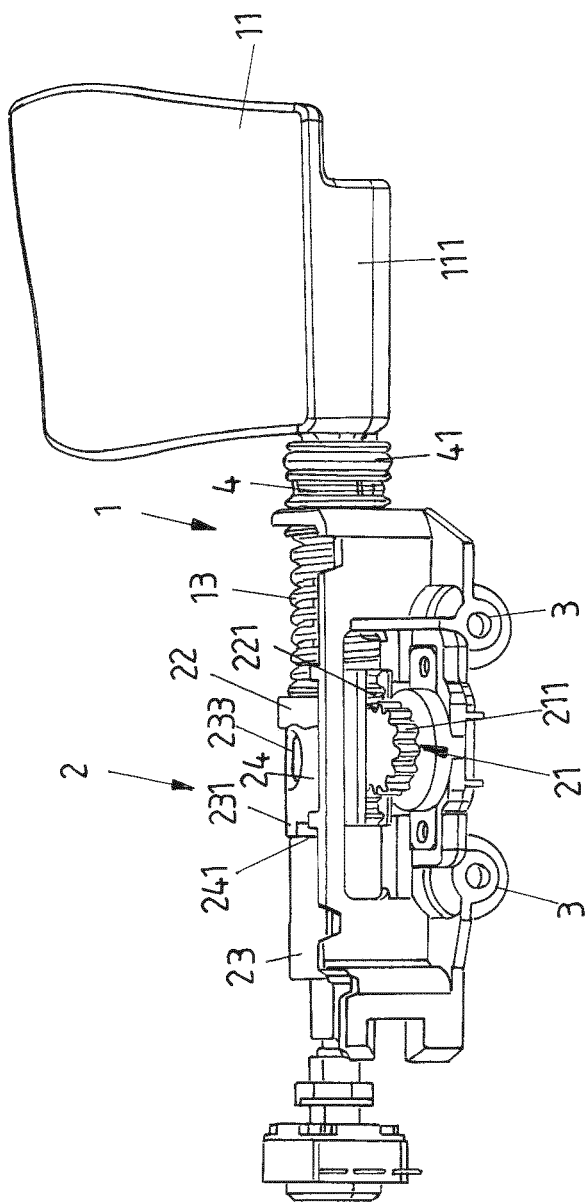
FIG. 2 the holding device of FIG. 1 in the closed position.

FIGS. 1 and 2 depict a holding device 1 according to an embodiment of the invention for use in a syringe pump (not shown). The holding device 1 comprises a rotatable holding member 11 which can be rotated from an open position (shown in FIG. 1) to a closed position (FIG. 2) in order to clamp a barrel of a syringe (not shown) against a fixed section of the syringe pump. The fixed section of the syringe pump may be a receptacle having, for example, a curved surface adapted to the cylindrical surface of the syringe barrel.

The holding member 11 similarly comprises a curved (concave) surface portion 111 for receiving a section of the syringe barrel. The holding member 11 is connected to a shaft 12, wherein for clamping the syringe barrel the holding member 11 is rotated about the axis of the shaft 12. Further, a coil spring 13 surrounding shaft 12 interacts with the holding member 11 such that the coil spring 13 is tensioned when the holding member 11 is rotated into the open position (shown in FIG. 1). Accordingly, the spring 13 supports the rotation of the holding member 11 into the closed position and biases the holding member 11 against the syringe barrel such that the syringe barrel is pressed against the fixed section of the syringe pump. In particular, the spring constant of the coil spring 13 is rather high such that a rather high force will be exerted on the syringe barrel to securely hold the barrel in place.

In order to avoid damage to the syringe barrel despite the high spring constant when the holding member 11 is pivoted into the closed position, the holding device 1 comprises a damping device 2 that slows down the rotation of the holding member 11 into the closed position.

The damping device 2 comprises a first toothed element in the form of a braked gear wheel 21 engaging a second toothed element in the form of a gear rack 22. More particularly, the gear rack 22 comprises a plurality of linearly arranged teeth 221 engaging circumferential teeth 211 of the gear wheel 21.

The holding device 1 further comprises a cam element consisting of a cam tube 23 and a specific part 24 arranged at the cam tube 23. As will be explained in more detail below with reference to FIG. 3, the cam tube 23 comprises an opening 232 receiving a protrusion (e.g. in the form of a radially extending pin 121 as exemplarily shown in FIG. 3) of shaft 12. The specific part 24 is arranged on a portion of the cam tube 23 that comprises the opening 232, wherein the specific part 24 is used to keep the pin 121 in good position (FIG. 2) (by means of a notch located at an ending of the specific part 24). During assembly of the holding device, the pin 121 is inserted into the opening 232 of cam tube 23 using an opening 233 of the specific part 24. Subsequently, the specific part 24 is turned relatively to the cam tube 23 into a final position to avoid losing the pin 121, i.e. in order to avoid that the pin 121 disengages from opening 232. In the final position, a protrusion 231 of the specific part 24 engages a corresponding recess of the cam tube 23.

When the shaft 12 (i.e. the holding member 11) is rotated, the pin 121 will push against an edge 2321 of the opening 232 such that a translation of the cam tube 23 parallel to the axis of shaft 12 is generated. The gear rack 22 is mounted to the specific part 24 such that when the cam tube 23 (and thus the specific part 24) moves linearly a translation of the gear rack 22 is generated. In particular, the cam tube 23 and thus the gear rack 22 will be moved towards the holding member 11 when the holding member 11 is moved into the open position and away from the holding member 11 when the holding member 11 is moved into the closed position. Thus, a rotation of the holding member 11 results in a rotation of the braked gear wheel 21, wherein the braked gear wheel 21 comprises a braking device that slows down the rotation of the braked gear wheel 21 and thus of the holding member 11. For example, the braking device comprises a viscous fluid slowing down the rotation of gear wheel 21 due to viscous forces. However, other mechanisms could be employed for slowing down the gear wheel 21 as set forth above.

It is also noted that instead of using a braked gear wheel 21, a (e.g. hollow cylindrical) friction element, a hydraulic jack or a pneumatic jack (not shown) might be provided, these components interacting with the shaft 12 in such a way that a translational movement of the shaft 12 and thus a rotation of the holding member 11 into the closed position is braked.

Moreover, the spring 13 may be connected to the cam tube 23 in such a way that it will be compressed (by the linearly moving cam tube 23) when the holding member 11 is rotated into the open position and relaxes when the holding member 11 is moved into the closed position.

It is noted that the gear rack 22 may be a separate part fixedly mounted to the specific part 24 (e.g. via a snap fitting connection, e.g. to the above-mentioned notch at the end of the specific part 24) such that it will move along with the cam tube 23 and the specific part 24. However, it is also possible that the gear rack 22 and the specific part 24 are integrally formed, i.e. as a single part. It is also noted that the holding device according to the invention may comprise attachment structures (such as attachment openings 3) for attaching the holding device to other parts of a syringe pump.

The holding device 1 moreover comprises a spacer 4 arranged between the spring 13 and the holding member 11. Further, a sealing ring 41 is arranged on the spacer 4, wherein the sealing ring 41 will be used to seal a section of the holding device 1 (in particular the damping device 2, the spring 13 and the cam tube 23) when the holding device 1 is installed in a syringe pump (see FIG. 4).

FIG. 3 shows the cam tube 23 without the specific part 24 and the gear rack 22. As already set forth above, the cam tube 23 comprises a recess in the form of the slit-like opening 232, wherein the radial pin 121 of shaft 12 protrudes into the opening 232. The opening 232 extends in a plane that is inclined (towards holding member 11) relative to the axis of shaft 12 such that the shaft pin 121 will engage a contact surface in the form of the edge 2321 of the opening 232 when the shaft 12 (i.e. the holding member 11) rotates.

More particularly, the pin 121 will engage a lower portion 2322 of the edge 2321 when the holding member 11 is rotated into the open position (as shown in FIG. 3), thereby pushing the cam tube 23 towards the holding member 11 against the spring 13. Conversely, when the holding member 11 is rotated into the closed position (i.e. upwards in FIG. 3) using the support of spring 13, the pin 121 will engage an upper portion 2323 of edge 2321 thereby pushing the cam tube 23 away from the holding member 11. Accordingly, the gear rack 22 (shown in FIG. 1) mounted to the cam tube 23 will move linearly away and towards the holding member 11, respectively.

FIG. 4 illustrates a syringe pump 10 including a holding device 1 according to the invention, in particular the holding device 1 illustrated in FIGS. 1 to 3. The barrel of a syringe (not shown) will be arranged in a receiving section 101 of the syringe pump 10, wherein the syringe barrel can be secured between the holding member 11 and a curved sidewall 102 of the receiving section 101. The other components of the holding device 1 are arranged within a housing section 103 of the receiving section 101.

The syringe pump 10 further comprises a display 104 and a movable gripper 105 for moving the piston of the syringe as in principle known in the art.

REFERENCE SIGNS

1 holding device
2 damping device
3 attachment opening
4 spacer
10 syringe pump
11 holding member
12 shaft
13 spring
21 braked gear wheel
22 gear rack
23 cam tube
24 specific part
41 sealing ring
101 receiving section
102 sidewall
103 housing section
104 display
105 gripper
111 curved surface
121 pin
211 teeth gear wheel
221 teeth gear rack
231 protrusion
232 opening
233 opening
241 contact surface
2321 edge of opening
2322 lower edge portion
2323 upper edge portion

The invention claimed is:

1. A holding device for a syringe pump, the holding device being configured for holding the barrel of a syringe and comprising:
   a shaft having a longitudinal axis,
   a rotatable holding member which is connected to the shaft and rotatable about the longitudinal axis of the shaft relative to a fixed section of the syringe pump from an open position wherein the syringe barrel is not secured between a portion of the rotatable holding member and the fixed section of the syringe pump into a closed position wherein the syringe barrel is secured between the portion of the rotatable holding member and the fixed section of the syringe pump,
   a damping device configured to dampen a rotation of the rotatable holding member about the longitudinal axis from the open position into the closed position; and
   a spring configured to bias the holding member against the syringe barrel, wherein the spring is a coil spring surrounding the shaft connected to the rotatable holding member.

2. A holding device for a syringe pump, the holding device being configured for holding the barrel of a syringe and comprising:
   a shaft having a longitudinal axis,
   a rotatable holding member which is connected to the shaft and rotatable about the longitudinal axis of the shaft relative to a fixed section of the syringe pump from an open position wherein the syringe barrel is not secured between a portion of the rotatable holding member and the fixed section of the syringe pump into a closed position wherein the syringe barrel is secured between the portion of the rotatable holding member and the fixed section of the syringe pump, and
   a damping device configured to dampen a rotation of the rotatable holding member about the longitudinal axis from the open position into the closed position,
   wherein the damping device comprises a first and a second toothed element in engagement with one another, and
   wherein the second toothed element moves linearly when the holding member is rotated from the open position into the closed position.

3. The holding device as claimed in claim 2, wherein the first toothed element is a gear wheel and the second toothed element is a gear rack.

4. A holding device for a syringe pump, the holding device being configured for holding the barrel of a syringe and comprising:
   a rotatable holding member which is rotatable relative to a fixed section of the syringe pump from an open position wherein the syringe barrel is not secured between a portion of the rotatable holding member and the fixed section of the syringe pump into a closed position wherein the syringe barrel is secured between the portion of the rotatable holding member and the fixed section of the syringe pump,
   a damping device configured to dampen the movement of the rotatable holding member from the open position into the closed position,
   the damping device comprising a first and a second toothed element in engagement with one another, the first toothed element being a gear wheel and the second toothed element being a gear rack, and the second toothed element moving linearly when the holding member is rotated from the open position into the closed position, and a shaft rotating along with the rotatable holding member and a cam element connected to the second toothed element, wherein the shaft engages the cam element in such a way that the cam element and thus the second toothed element is linearly moved when the rotatable holding member is rotated from the open position into the closed position.

5. The holding device as claimed in claim 4, wherein the shaft comprises a protrusion engaging a contact surface of the cam element.

6. The holding device as claimed in claim 5, wherein the protrusion extends radially.

7. The holding device as claimed in claim 6, wherein the contact surface is orientated obliquely with respect to the axis of the shaft.

8. The holding device as claimed in claim 7, wherein the contact surface extends under an angle of about 45° with respect to axis of the shaft.

9. The holding device as claimed in claim 5, wherein the cam element comprises a hollow body at least partially surrounding the shaft, wherein the contact surface is formed by an edge of a recess in the hollow body.

10. The holding device as claimed in claim 1, wherein the damping device comprises a friction element, a hydraulic jack or a pneumatic jack.

11. The holding device as claimed in claim 1, wherein the holding member comprises a concave surface portion.

12. A syringe pump comprising a holding device as claimed in claim 1.

13. The holding device as claimed in claim 1, wherein the longitudinal axis of the shaft is configured to be parallel to the syringe barrel with the syringe barrel secured between the portion of the rotatable holding member and the fixed section of the syringe pump.

14. The holding device as claimed in claim 2, further comprising a spring configured to bias the holding member against the syringe barrel, wherein the spring is a coil spring surrounding the shaft connected to the rotatable holding member.

15. The holding device as claimed in claim 2, wherein the holding member comprises a concave surface portion.

16. A syringe pump comprising a holding device as claimed in claim 2.

17. The holding device as claimed in claim 4, further comprising a spring configured to bias the holding member against the syringe barrel, wherein the spring is a coil spring surrounding the shaft.

18. The holding device as claimed in claim 4, wherein the holding member comprises a concave surface portion.

19. A syringe pump comprising a holding device as claimed in claim 4.

* * * * *